United States Patent [19]

Goldsberry

[11] Patent Number: Plant 6,555

[45] Date of Patent: Jan. 24, 1989

[54] DWARF CARNATION PLANT CRESTONE

[75] Inventor: Kenneth L. Goldsberry, Fort Collins, Colo.

[73] Assignee: Colorado State University Research Foundation, Fort Collins, Colo.

[21] Appl. No.: 45,595

[22] Filed: May 4, 1987

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Edwin L. Spangler, Jr.

[57] ABSTRACT

A carnation plant known by the cultivar name Crestone was developed through a breeding program and is particularly characterized as to uniqueness by its dwarf growth habit and the following combined characteristics: upon pinching a rooted cutting, forms 3 to 5 lateral stems 18 to 25 cm long, each developing a terminal flower and 4 to 6 lateral buds which open intermittently after the terminal flowers seneses; white flowers 4.5 to 5.5 cm in diameter have a purple picotee edge, but without fragrance; can be grown under specified environmental conditions either as a single pinched plant per 10 cm pot or 3 pinched plants per 13 cm pot, which results in an ideal new flowering house plant.

1 Drawing Sheet

My present invention relates to a new and distinct dwarf cultivar of *Dianthus caryophyllus* Linn. identified as plant 85-230-3 and given the name Crestone.

Crestone is a product of a breeding program started by me at Colorado State University in 1974, using commercially available semi dwarf germplasm, crossing selected unnamed seedlings and incorporating various known carnation germplasm with an objective of creating dwarf carnation cultivars that could be asexually produced for commercial use, in controlled environments, as flowering house plants.

Crestone was originated from a cross made in a controlled breeding program at the Horticulture Department, W. D. Holley Plant Environmental Research Center, Colorado State University, Fort Collins, Colo. using the unnamed seed parent 83-56-6 and an unnamed pollen parent 83-20-14, also developed by the present inventor.

Crestone was discovered and selected as one flowering plant within the progeny of the stated cross by Kenneth L. Goldsberry on July 28, 1985 in a controlled environment in Fort Collins, Colo.

The first act of asexual reproduction of Crestone was accomplished when vegetative cutting's were taken, by the inventor, from the initial selection on Sept. 5, 1985 in a controlled environment in Fort Collins, Colo. The initial rooting of the cuttings and performance of the resulting plants has demonstrated that the distinctive characteristics of this new cultivar Crestone, here in disclosed, appear to be firmly fixed and hold true from generation to generation.

Crestone has not been observed under all possible environmental conditions. The phenotype may vary significantly with variation in the production environment including irrigation regimes, temperature, light intensity, day length and nutritional programs. It has been observed and evaluated, from a rooted cutting to a mature plant while being grown in Fort Collins and Denver, Colo. and Encintias and Salinas, Calif. under greenhouse conditions, which approximate those generally used in commercial practice.

The following traits, which have been repeatedly observed, characterize Crestone and distinguishes it as a new and distinct dwarf carnation cultivar:

1. Somatic chromosome is 2n=30.
2. A double type flower, similar to commercial cut flower spray types.
3 Flower size ranges from 45 to 55 mm in diameter.
4 White flower color with purple picotee edge.
5. Medium flowering response on a scale of early, medium or late flowering.
6. Three to five lateral shoots develop following a pinch of the main stem.
7. The terminal flower, four to six secondary buds and two to three tertiary buds from one each lateral stem. As the old flowers senese, the secondary buds continue to open, the tertiary buds usually abort.
8. Peduncle length on a single stem varies between 1 to 10.3 cm.
9. Plant height ranges between 19 to 23 cm.
10. The flowers have no fragrance.

There are no dwarf carnation cultivars, for house plant use, presently developed and known to the inventor.

The accompanying colored photographs taken on Oct. 26, 1986, using an 18 percent Kodak photographic gray card as a color base, illustrate in perspective view and the overall appearance of Crestone (85-230-3) grown in 10 cm (single plant and 15 cm (3 plants) azalea pots. The buds, inflorescence, stem, foliage characteristics and color of Crestone are typical and true as possible with illustrations of this type.

The following detailed description of my new dwarf carnation cultivar are based upon observations of greenhouse grown plants made in 1986 at Fort Collins, Colo. The color values were determined in a standard color viewing booth with a 5000° K. florescent light source using reference developed and published by The Royal Horticultural Society, London, England.

PLANT CHARACTERISTICS

Origin: Seedling selection.

Parentage:

*Seed parent.*—Selected unnamed seedling, 83-56-6 (Goldsberry).

*Pollen parent.*—Selected unnamed seedling 83-20-14 (Goldsberry).

Classification:

*Botanic.*—*Dianthus caryophyllus* Linn. cv. Crestone.

*Commercial.*—Dwarf carnation for pot plant production.

Propagation: Vegetative cuttings, 6 to 8 cm. in length initiate visible roots in 8 to 10 days in the winter and 5 to 8 during the summer, when rooted under mist in a rooting medium temperature of 20° C. A quality rooted cutting with an abundance of roots, is usually ready to plant in 15 days in the summer and 18 to 20 in the winter.

Growth habit: Four to six lateral shoots form naturally, but are accelerated by removing the terminal portion of the main stem, at the sixth or seventh node from the top, resulting in a compact, bushy and strong up right plant. Some basal branches may elongate enough to place apical buds on planes 2–5 cm above the terminal flowers of the initial stems.

Stems: Numerous lateral branches form close to the base of the plant and vary in length from 18–25 cm, having 8 to 11 nodes with opposite leaves. A reproductive bud usually forms at each upper 5 nodes. Shoots forming at the sixth to eleventh node below the terminal flower, usually develop into another flower stem in proper environmental conditions. All stems have a blue-grey glaucous condition, approximating 189A in color.

Foliage: Leaves are abundant and typical of the commercial carnation type. The leaves at the sixth and seventh nodes from the top of each stem range in length from 10.0 to 13.8 cm and the widest leaves occur at the forth and fifth nodes and have an average width of 7.6 mm, but are progressively smaller above and below these positions. Both the upper and lower sides of the leaves are dark green and have a blue-grey glaucous condition. The color of both surfaces is identified as 189A with the surface bloom present and 139A when it is removed.

INFLORESCENCE CHARACTERISTICS

Buds: Terminal buds average 2.6 cm in length just prior to opening and the secondary buds 2.5 to 2.6 cm. The average bud circumference ranges from 4.9 cm for the terminal and secondary buds 4.6 cm at the first sign of petal color. Tertiary buds usually develop on the upper most secondary stems. Buds are oval in shape and pointed.

Sequence of development: The terminal bud on each stem will show color before any secondary bud color is visible. The flowering of the secondary buds is irregular on each stem. In the proper environments, new flower bearing shoots emerge from the sixth to eleventh nodes below the terminal flower and at the base of the plant, creating a perpetual flowering plant.

Flowering response: A plant pinched 2 to 3 weeks after planting will flower 12 to 13 weeks following the pinch from a October 1 plant date and 9 to 10 weeks from a June 1 date in Fort Collins, Colo. when growing temperatures approximate 11° C. at night and 17° C. during the day.

Inflorescence type: Each initial stem is a semi-compound spray with a terminal bud, 4 to 6 secondary and 1 to 3 tertiary buds and three to 6 lateral shoots.

Number of buds and flowers per stem: Each stem has a terminal flower that develops along with the upper most, of the 4 to 6 lateral secondary and 1 to 3 tertiary buds; new flowering shoots usually form at the sixth to eleven nodes of each initial stem resulting in an average of 5.8 flowers per stem. The secondary buds open intermittently down the stem.

Peduncle length: The length of the peduncles range from 1 cm for the top secondary bud to 10.3 cm for the fifth bud from the top on each stem, when the terminal flower is in prime condition. The peduncle length for the tertiary buds varies from 1 to 1.3 cm.

Peduncle strength: Strong, holds flowers erect during all growing seasons; degree of brittleness is related to environmental conditions.

Flower:

*Size.*—Terminal flowers range in size from 5.0 to 6.0 cm in diameter and the secondaries 4.5 to 5.5 cm depending on the environment.

*Type.*—Commercial double with 42 to 75 moderately serrated petals with an average length of 4.1 cm and 2.5 cm wide in the terminal flower. The secondary flowers have 37 to 49 petals with an average length of 3.9 cm and are 2.1 cm wide. The tertiary buds do not open.

*Form.*—Sub hemispherical in longitudinal section with the petals adjacent to the calyx, slightly reflexed at maturity. Seldom splits.

Corolla color: General tonality at a distance of 1 meter: white with a 61A picotee margin. Upper petal surface: A purple (61A) picotee edge with a few 61A flecks extending from the margin. Lower petal surface: Same as the upper surface.

Keeping quality: In the greenhouse, individual flower remain aesthetically pleasing up to 6 days; in the home 8 to 13 days with room temperatures of 17° C. and high, natural light intensity.

Fragrance: None.

Reproductive organs:

*Androecium.*—Typical carnation except has aborted 26–42 filaments, no anthers or pollen.

*Gynoecuim.*—Typical of carnation in all respects; pistil is 1.0 to 1.1 cm in length and has 2 to 3 styles and stigmas. The stigmas are white at all stages of flower maturity.

Disease resistance: The plant has been found free of pathogen races currently associated with standard carnation cultivars, including the wilts and Etched Ring or Fleck viruses.

I claim:

1. A new and distinct cultivar of *Dianthus caryophyllus,* Linn, identified as 85-230-3 and known as Crestone and substantially as herein described and illustrated.

* * * * *

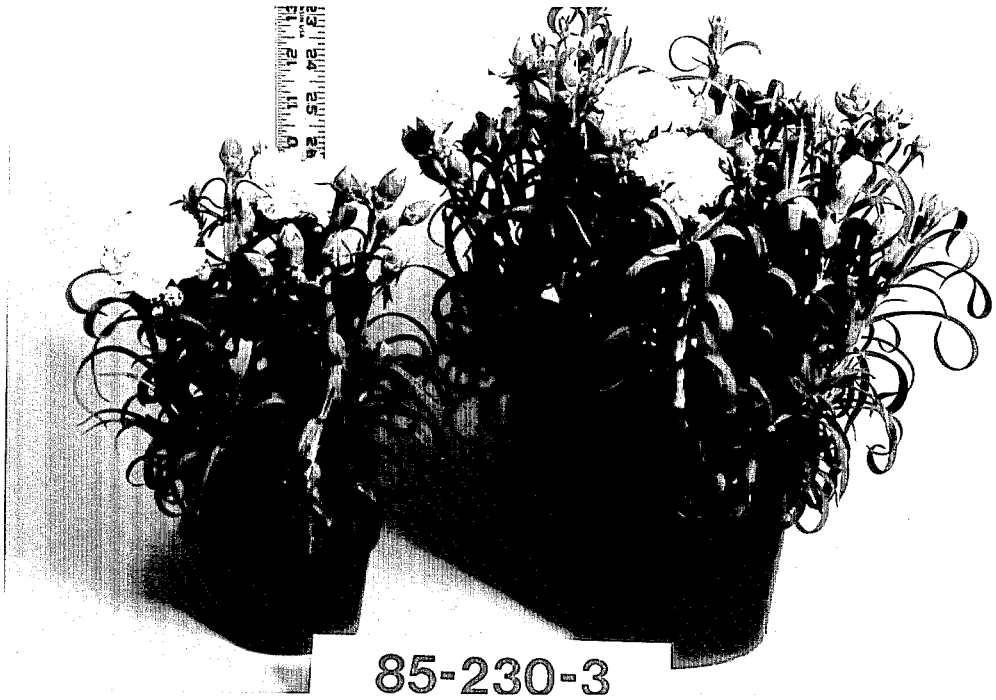
85-230-3
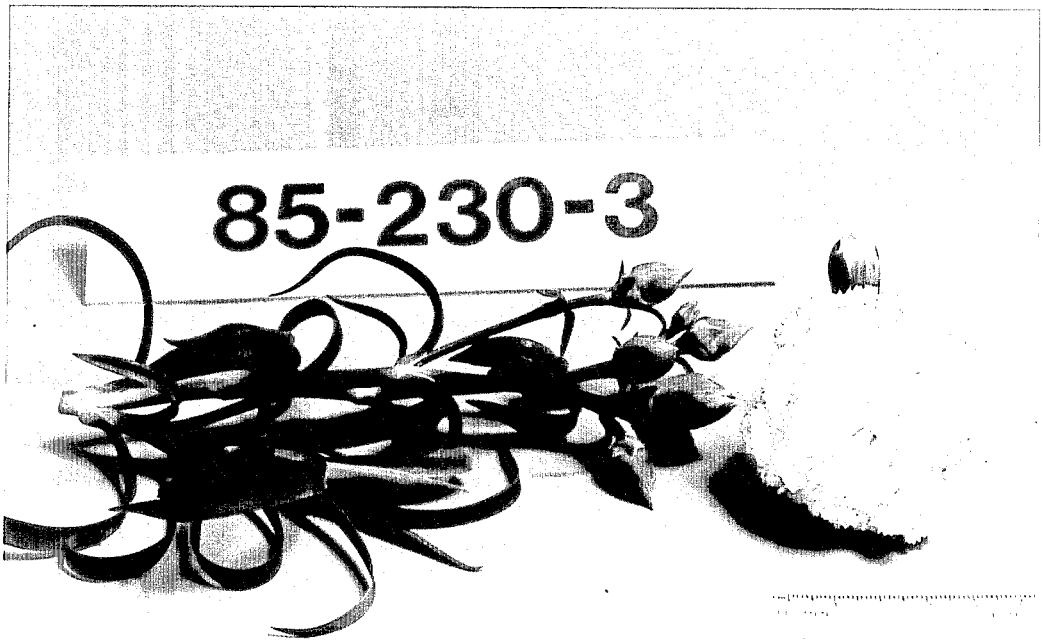
85-230-3